United States Patent [19]

Buckle et al.

[11] Patent Number: 5,254,557

[45] Date of Patent: Oct. 19, 1993

[54] COMPOUND AND TREATMENT

[75] Inventors: Derek R. Buckle; David G. Smith, both of Epsom; Frederick Cassidy, Harlow, all of England

[73] Assignee: Beecham Group p.l.c., England

[21] Appl. No.: 892,619

[22] Filed: Jun. 1, 1992

Related U.S. Application Data

[63] Continuation of Ser. No. 458,636, Jan. 9, 1990, abandoned.

[30] Foreign Application Priority Data

May 9, 1988 [GB] United Kingdom ............... 8810929
Nov. 1, 1988 [GB] United Kingdom ............. 88255088

[51] Int. Cl.⁵ ................. C07D 401/14; C07D 403/14; A61K 31/44; A61K 31/505
[52] U.S. Cl. ..................... 514/269; 514/254; 514/274; 514/278; 514/302; 544/230; 544/238; 544/298; 544/316; 544/319; 544/405; 546/15; 546/115; 546/116
[58] Field of Search ............... 514/278, 302, 254, 269, 514/274; 546/15, 116, 115; 544/230, 238, 298, 316, 319, 405

[56] References Cited

U.S. PATENT DOCUMENTS 4,931,454  6/1990  Baumgarth et al. ............... 514/254

FOREIGN PATENT DOCUMENTS 0176689  4/1986  European Pat. Off. .
205292  12/1986  European Pat. Off. .
0273262  12/1987  European Pat. Off. .
0308792  9/1988  European Pat. Off. .
0296975  12/1988  European Pat. Off. .

Primary Examiner—John M. Ford
Attorney, Agent, or Firm—Rosenman & Colin

[57] ABSTRACT

A compound of formula (IA) in the form of a pharmaceutically acceptable microfine powder is disclosed.

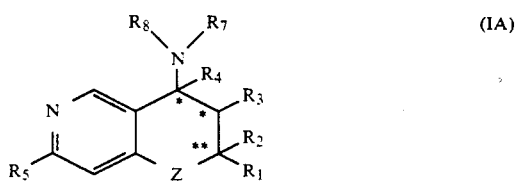

(IA)

26 Claims, No Drawings

COMPOUND AND TREATMENT

This application is a continuation of Ser. No. 07/458,636, filed Jan. 9, 1990, now abandoned.

This invention relates to certain 4-unsaturated heterocyclyl benzopyran derivatives, having smooth muscle relaxant activity, to processes for their preparation, to compositions containing such compounds and to the use of such compounds and compositions in medicine. The invention also, particularly, relates to a method for the treatment of reversible airways obstruction and asthma, especially by inhaled administration, and to substances and compositions used in such method.

EP-A-76075, 93535, 95316, 107423, 120426, 126311, 126350, 126367 and 138134 describe certain benzopyran derivatives having inter alia antihypertensive activity. EP-A-176689 also discloses that certain benzopyran derivatives are useful for the treatment of inter alia disorders of the respiratory system.

EP-A-205292 discloses certain pyrano [3,2-c]pyridine derivatives having inter alia blood pressure lowering activity.

EP-A-273262 discloses certain chroman derivatives including trans-6-cyano-3,4-dihydro-2,2-dimethyl-4-(2(1H)-pyridon-1-yl)-2H-1-benzopyran-3-ol, 6-cyano-2,2-dimethyl-4-(2(1H)-pyridon-1-yl)-2H-1-benzopyran, trans-3,4-dihydro-2,2-dimethyl-6-trifluoromethyl-4-(2(1H)-pyridon-1-yl)-2H-1-benzopyran-3-ol, 2,2-dimethyl-6-trifluoromethyl-4-(2(1H)-pyridon-1-yl)-2H-1-benzopyran and trans-6-cyano-3,4-dihydro-2,2-dimethyl-4-(6(1H)-pyrimidon-1-yl)-2H-1-benzopyran-3-ol. These compounds are disclosed as being useful in the treatment of diseases of the cardiovascular system and diseases associated with high blood pressure. They are also disclosed as having a relaxing action on various smooth muscle organs (the gastro-intestinal tract, the respiratory system and the uterus). Having regard to the European Patent Convention (EPC), the disclosures of EP-A-273262 are relevant to the present application via Article 54(3) EPC but not via Article 54(2) EPC nor via Article 56 EPC.

EP-A-296975 discloses certain chroman derivatives including trans-6-cyano-3,4-dihydro-2,2-dimethyl-4-(2(1H)-pyridon-1-yl)-2H-1-benzopyran-3-ol and trans-3,4-dihydro-2,2-dimethyl-6-trifluoromethyl-(2(1H)-pyridon-1-yl)-2H-1-benzopyran-3-ol. These compounds are disclosed as having hypertensive and antiarrythmic activity. Having regard to the European Patent Convention (EPC) the disclosures of EP-A-296276 are relevant to the present application via Article 54(3) EPC but not via Article 54(2) EPC nor via Article 56 EPC.

EP-A-308792 discloses certain azachroman derivatives including trans-3,4-dihydro-2,2-dimethyl-4-(2(1H)-pyridon-1-yl)-2H-pyrano[3,2-c]pyridine-3-ol), 2,2-dimethyl-4-(2(1H)-pyridon-1-yl)-2H-pyrano[3,2-c]pyridine and trans-3,4-dihydro-2,2-dimethyl-4-(2(1H)-pyrimidinon-1-yl)-2H-pyrano[3,2-c]pyridine-3-ol. These compounds are disclosed as being useful in the treatment of diseases of the cardiovascular system and diseases associated with high blood pressure. They are also disclosed as having a relaxing action on various smooth muscle organs (the gastro-intestinal tract, the respiratory system and the uterus). Having regard to the European Patent Convention (EPC) the disclosures of EP-A-308792 are relevant to the present application via Article 54(3) EPC but not via Article 54(2) EPC nor via Article 56 EPC.

A group of 4-unsaturated heterocyclyl benzopyran derivatives has now been discovered which surprisingly has smooth muscle relaxant activity, and such compounds are therefore potentially useful as bronchodilators in the treatment of disorders of the respiratory tract, such as reversible airways obstruction and asthma, and also in the treatment of hypertension. Such compounds are also indicated as of potential use in the treatment of disorders associated with smooth muscle contraction of the gastro-intestinal tract, uterus or the urinary tract including the ureter. Such disorders respectively include irritable bowel syndrome and diverticular disease; premature labour; incontinence; renal cholic and disorders associated with the passage of kidney stones. They are also indicated as of potential use in the treatment of cardiovascular disorders other than hypertension, such as congestive heart failure, angina, peripheral vascular disease and cerebral vascularidisease; and also in the treatment and/or prophylaxis of disorders associated with pulmonary hypertension and of disorders associated with right heart failure.

A particular group of these compounds has also surprisingly been discovered to be of particular benefit for the treatment of reversible airways obstruction and asthma, especially when administered by inhaled administration. These compounds are also of potential use in the treatment of irritable bowel syndrome and diverticular disease; premature labour; incontinence; renal cholic and disorders associated with the passage of kidney stones. They are also indicated to be of potential use in the treatment and/or propylaxis of disorders associated with pulmonary hypertension and of disorders associated with right heart failure.

Accordingly, in one aspect, the present invention provides a compound of formula (I):

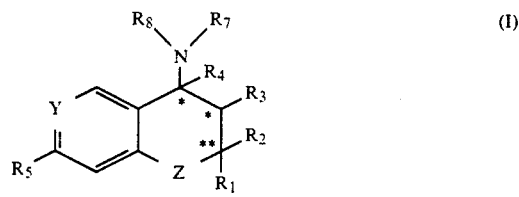

or, where appropriate, a pharmaceutically acceptable salt thereof, or a pharmaceutically acceptable solvate thereof wherein:

Y represents N or $N^+-O^-$ or a moiety $CR_6$ wherein $R_6$ is as defined below;

Z represents O, $CH_2$, NR, or $S(O)_n$ wherein n represents 0, 1 or 2;

R represents hydrogen, alkyl or alkylcarbonyl;

$R_1$ and $R_2$ independently represent hydrogen or alkyl; or $R_1$ and $R_2$ together represent a polymethylene moiety;

$R_3$ represents hydrogen, hydroxy, alkoxy or acyloxy;

$R_4$ represents hydrogen or $R_3$ and $R_4$ together represent a bond;

when Y is N or $N^+-O^-$, $R_5$ is hydrogen or, when Y is $CR_6$, either one of $R_5$ and $R_6$ is hydrogen and the other is selected from the group consisting of: alkylcarbonyl, alkoxycarbonyl, alkylcarbonyloxy, alkylhydroxymethyl, nitro, cyano, halogen, trifluoromethyl, alkylsulphinyl, alkylsulphonyl, alkoxysulphinyl, alkoxysulphonyl, alkylcarbonylamino, alkoxycarbonylamino, alkyl-thiocarbonyl, alkoxythiocarbonyl, alkyl-thiocarbonyloxy, alkyl-thiomethyl, formyl or aminosulphinyl, aminosulphonyl or aminocarbonyl, the amino moiety being optionally substituted by one or two alkyl groups, or alkylsulphinylamino, alkylsulphonylamino, alkoxysulphinylamino or alkoxysulphonylamino or ethenyl terminally substituted by alkylcarbonyl, nitro or cyano, or —C(alkyl)NOH or —C(alkyl)NNH$_2$; or one of R$_5$ and R$_6$ is nitro, cyano or C$_{1-3}$ alkylcarbonyl and the other is methoxy or amino optionally substituted by one or two alkyl or by C$_{2-7}$ alkanoyl; or R$_5$ is hydrogen and R$_6$ is alkyl or cycloalkyl; and wherein R$_7$ and R$_8$ together with the nitrogen atom to which they are attached form a 6-membered, substituted or unsubstituted, unsaturated heterocyclic ring, the ring being a single ring and comprising up to 2 further nitrogen atoms, and also comprising the carbon atom of a group C=X wherein X represents O or S; providing that formula (I) does not encompass trans-6-cyano-3,4-dihydro-2,2-dimethyl-4-(2(1H)-pyridon-1-yl)-2H-1-benzopyran-3-ol, 6-cyano-2,2-dimethyl,4-(2(1H)-pyridon-1-yl)-2H-1-benzopyran, trans-3,4-dihydro-2,2-dimethyl-6-trifluoromethyl-4-(2(1H)-pyridon-1-yl)-2H-1-benzopyran-3-ol, 2,2-dimethyl-6-trifluoromethyl-4-(2(1H)-pyridon-1-yl)-2H-1-benzopyran, trans-6-cyano-3,4-dihydro-2,2-dimethyl-(6(1H)-pyrimidon-1-yl)-2H-1-benzopyran-3-ol, trans-3,4-dihydro-2,2-dimethyl-4-(2(1H)-pyridon-1-yl)-2H-pyrano[3,2-c]pyridine-3-ol, 2,2-dimethyl-4-(2(1H)-pyridon-1-yl)-2H-pyrano[3,2-c]pyridine and trans-3,4-dihydro-2,2-dimethyl-4-(2(1H)-pyrimidinon-1-yl)-2H-pyrano[3,2-c]pyridine-3-ol.

Suitably, R$_7$ and R$_8$ together with the nitrogen atom to which they are attached, form a substituted or unsubstituted pyridonyl group or a substituted or unsubstituted thiopyridonyl group.

Suitably the moiety R$_8$.N.R$_7$ represents substituted or unsubstituted pyridonyl, favourably unsubstituted pyridonyl.

A favoured pyridonyl group is a 2-pyridon-1-yl group.

A favoured pyridonyl group is a 4-pyridon-1-yl group.

Suitably, when the moiety R$_7$.N.R$_8$ comprises further nitrogen atoms, it comprises 1 further nitrogen atom.

Suitably, R$_8$.N.R$_7$ represents substituted or unsubstituted pyrimidinonyl or thiopyrimidinonyl, favourably unsubstituted pyrimidinonyl or thiopyrimidinonyl, in particular pyrimidinonyl. A favoured pyrimidinonyl group is a 4(1H)-pyrimidinon-1-yl a 6(1H)-pyrimidinon-1-yl or a 2(1H)-pyrimidinon-1-yl group.

A suitable substituent for the group R$_8$.N.R$_7$, and especially for the pyridonyl group, or the thiopyridonyl group is an alkyl group, suitably a C$_{1-6}$ alkyl group, such as a methyl group.

Preferably, Y represents N or N$^+$—O$^-$.

In one subgroup of compounds, Y represents N$^+$—O$^-$.

Most preferably, Y represents N.

Accordingly in a most preferred aspect of the present invention there is provided a compound of formula (IA):

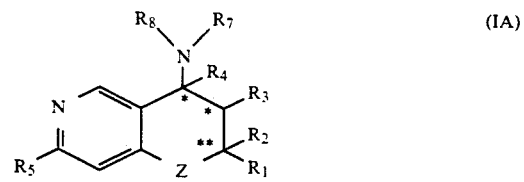

or, where appropriate, a pharmaceutically acceptable salt thereof, or a pharmaceutically acceptable solvate thereof, wherein:

Z represents O, CH$_2$, NR or S(O)$_n$ wherein n represents 0, 1 or 2;
R represents hydrogen, alkyl or alkylcarbonyl;
R$_1$ and R$_2$ independently represent hydrogen or alkyl; or
R$_1$ and R$_2$ together represent a polymethylene moiety;
R$_3$ represents hydrogen, hydroxy, alkoxy or acyloxy;
R$_4$ represents hydrogen or R$_3$ and R$_4$ together represent a bond; and wherein R$_7$ and R$_8$ together with the nitrogen atom to which they are attached form a 6-membered, substituted or unsubstituted, unsaturated heterocyclic ring, the ring being a single ring and comprising up to 2 further nitrogen atoms, and also comprising the carbon atom of a group C=X wherein X represents O or S.

One subclass of formula (I) includes those compounds wherein:

Y represents N or N$^+$—O$^-$ or a moiety CR$_6$ wherein R$_6$ is as defined below;
Z represents O, CH$_2$ or NR;
R represents hydrogen, C$_{1-6}$ alkyl or C$_{1-6}$ alkylcarbonyl;
R$_1$ and R$_2$ independently represent hydrogen or C$_{1-6}$ alkyl; or R$_1$ and R$_2$ together represent a C$_{2-7}$ polymethylene moiety;
R$_3$ represents hydrogen, hydroxy, C$_{1-6}$ alkoxy or C$_{1-7}$ acyloxy;
R$_4$ represents hydrogen or R$_3$ and R$_4$ together represent a bond;

when Y is N or N$^+$—O$^-$, R$_5$ is hydrogen or, when Y is CR$_6$, either one of R$_5$ and R$_6$ is hydrogen and the other is selected from the group consisting of: C$_{1-6}$ alkylcarbonyl, C$_{1-6}$ alkoxycarbonyl, C$_{1-6}$ alkylcarbonyloxy, C$_{1-6}$ alkylhydroxymethyl, nitro, cyano, chloro, trifluoromethyl, C$_{1-6}$ alkylsulphinyl, C$_{1-6}$ alkylsulphonyl, C$_{1-6}$ alkoxysulphinyl, C$_{1-6}$ alkoxysulphonyl, C$_{1-6}$ alkylcarbonylamino, C$_{1-6}$ alkoxycarbonylamino, C$_{1-6}$ alkyl-thiocarbonyl, C$_{1-6}$ alkoxy-thiocarbonyl, C$_{1-6}$ alkyl-thiocarbonyloxy, C$_{1-6}$ alkyl-thiomethyl, formyl or aminosulphinyl, aminosulphonyl or aminocarbonyl, the amino moiety being optionally substituted by one or two C$_{1-6}$ alkyl groups, or C$_{1-6}$ alkylsulphinylamino, C$_{1-6}$ alkylsulphonylamino C$_{1-6}$ alkoxysulphinylamino or C$_{1-6}$ alkoxysulphonylamino or ethenyl terminally substituted by C$_{1-6}$ alkylcarbonyl, nitro or cyano, or —C(C$_{1-6}$ alkyl)-NOH or —C(C$_{1-6}$ alkyl)NNH$_2$; or one of R$_5$ and R$_6$ is nitro, cyano or C$_{1-3}$ alkylcarbonyl and the other is methoxy or amino optionally substituted by one or two C$_{1-6}$ alkyl or by C$_{2-7}$ alkanoyl; or R$_5$ is hydrogen and R$_6$ is C$_{1-6}$ alkyl or C$_{3-8}$ cycloalkyl; and R$_7$ and R$_8$, together with the nitrogen atom to which they are attached, form a substituted or unsubstituted pyridonyl group or a substituted or unsubstituted thiopyridonyl group.

A subclass of formula (I) includes those compounds wherein Z represents CH$_2$, NR or S(O)$_n$ wherein n represents 0, 1 or 2, a further subclass being those wherein Z represents $CH_2$ or NR, yet a further subclass being those wherein Z represents $CH_2$.

Favourably however, Z represents O.

A subclass of formula (I) includes those compounds wherein $R_3$ and $R_4$ each represent hydrogen or wherein $R_3$ represents alkoxy and $R_4$ represents hydrogen.

Suitably however, $R_3$ represents hydroxy and $R_4$ represents hydrogen.

Preferably, $R_3$ and $R_4$ together represent a bond.

In particular should be mentioned those compounds wherein Y represents N or $N^+$—$O^-$ (especially N) and $R_3$ and $R_4$ together represent a bond.

A subclass of formula (I) includes those compounds wherein one of $R_5$ or $R_6$ represents hydrogen and the other represents alkylhydroxymethyl or alkylthiomethyl or ethenyl terminally substituted by alkylcarbonyl, nitro or cyano or —C(alkyl)NOH or —C(alkyl)NNH$_2$.

A subclass of formula (I) includes those compounds wherein one of $R_5$ or $R_6$ represents methoxy and the other represents nitro, cyano or $C_{1-3}$ alkylcarbonyl.

A subclass of formula (I) includes those compounds wherein $R_5$ is hydrogen and $R_6$ represents cycloalkyl. A subclass of formula (I) includes those compounds wherein $R_7.N.R_8$ represents a 6-membered, substituted or unsubstituted, unsaturated heterocyclic ring, the ring being a single ring and comprising up to 2 further nitrogen atoms, and also comprising the carbon atom of a group C=X wherein X represents O or S; providing that $R_7.N.R_8$ does not represent 1H-2-pyridon-1-yl, 1H-6-pyridazinon-1-yl, 1H-2-pyrimidinon-1-yl, 1H-6-pyrimidinon-1-yl, 1H-2-pyrazinon-1-yl or 1H-2-thiopyridon-1-yl radical which is unsubstituted or mono- or di substituted by A, F, Cl, Br, I, OH, OA, OAc, $NO_2$, $NH_2$, AcNH, HOOC and/or AOOC, it also being possible for these radicals to be partly hydrogenated, wherein A is alkyl with 1-6 C atoms and Ac is alkanoyl with 1-8 C atoms or aroyl with 7-11 C atoms or a group:

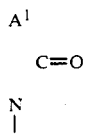

in which:

$A^1$, between N and CO, represents the group —CH=CH—E=CH— or the group

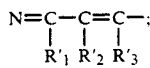

in which

E represents a nitrogen atom or a group C($R'_4$);

$R'_1$ represents hydrogen, a methyl group or a hydroxyl group and $R'_2$ and $R'_3$ each independently represent hydrogen or a methyl group, it being possible for only one of the substituents $R'_1$, $R'_2$ and $R'_3$ to be methyl; and $R'_4$ represents a hydrogen atom, a halogen atom, a methyl group or a hydroxyl group.

A subclass of formula (I) includes those compounds wherein $R_7.N.R_8$ represents 4(1H)-pyrimidinon-1-yl.

A subclass of formula (I) includes those compounds wherein $R_7.N.R_8$ is 4(1H)-thiopyrimidinon-1-yl.

A subclass of formula (I) includes those compounds wherein $R_7.N.R_8$ represents thiopyridonyl.

A subclass of formula (I) includes those compounds wherein $R_7.N.R_8$ represents 4-pyridon-1-yl.

A further subclass of formula (I) includes those compounds wherein $R_1$, $R_2$, $R_3$, $R_4$, $R_5$, $R_6$, $R_7$, $R_8$, Y and Z are as defined in relation to formula (I) providing that when Z represents O, $R_1$ and $R_2$ both represent $C_{1-6}$ alkyl; $R_3$ represents hydroxyl or $R_3$ and $R_4$ each represent a bond; one of $R_5$ or $R_6$ represents hydrogen and the other represents acetyl, $C_{1-6}$-alkoxycarbonyl, nitro, cyano, halogen or $CF_3$; and $R_7$ and $R_8$ together with the nitrogen atom to which they are attached, form a substituted or unsubstituted pyridonyl group or a substituted or unsubstituted thiopyridonyl group; then Y must represent N or $N^+$—$O^-$.

Preferably, $R_1$ and $R_2$ are both $C_{1-6}$ alkyl, and in particular $R_1$ and $R_2$ are both methyl.

When $R_3$ is $C_{1-6}$ alkoxy and $R_4$ is hydrogen, preferred examples of $R_3$ include methoxy and ethoxy, of which methoxy is more preferred. When $R_3$ is $C_{1-7}$ acyloxy and $R_4$ is hydrogen, a preferred class of $R_3$ is unsubstituted carboxylic acyloxy, such as unsubstituted aliphatic acyloxy. However, it is more preferred that $R_3$ and $R_4$ together are a bond, or that $R_3$ and $R_4$ are both hydrogen, or in particular, that $R_3$ is hydroxy and $R_4$ is hydrogen.

When Y represents $CR_6$, $R_6$ is preferably selected from the class of $C_{1-6}$ alkyl, $C_{3-8}$ cycloalkyl, $C_{1-6}$ alkylcarbonyl, $C_{1-6}$ alkoxycarbonyl, trifluoromethyl, nitro or cyano, especially when $R_5$ is hydrogen.

In particular, $R_6$ may be acetyl, trifluoromethyl, nitro, cyano, methyl, ethyl, isopropyl or cyclopentyl.

When one of $R_5$ and $R_6$ represents nitro, trifluoromethyl, cyano or $C_{1-3}$ alkylcarbonyl the other is preferably hydrogen.

The alkyl group or the alkyl moiety of an alkyl-containing group represented by $R^5$ or $R^6$ is preferably ethyl.

Particular examples of compounds of formula (I) include the compounds prepared in the Examples described hereinafter, hence particular examples of compounds of formula (IA) include the relevant examples described hereinafter.

Suitable pharmaceutically acceptable salts of the compounds of formula (I) include acid addition salts and salts of carboxy groups.

Examples of pharmaceutically acceptable acid addition salts of the compounds of formula (I) include acid addition salts of optionally substituted amino groups, such as the hydrochloride and hydrobromide salts. Such a salifiable group may form part of an $R_5$ group. It will also be appreciated that when Y in the compound of formula (I) represents N, then the resulting pyridine moiety may yield acid addition salts, such as the hydrochloride, hydrobromide malonate or methanesulphonate salts, an example being the malonate.

Examples of pharmaceutically acceptable salts of carboxy groups include metal salts, such as alkali metal salts, or optionally substituted ammonium salts.

The compounds of formula (I) may also exist in the form of solvates, preferably hydrates, and the invention extends to such solvates. In a further aspect the present invention also extends to include the solvates of such of the compounds which are excluded from formula (I).

The carbon atoms of formulae (I) and (IA) marked with an asterisk "*" are chiral carbon atoms when $R_3$ and $R_4$ do not represent a bond and, for the ring carbon atom attached to $R_3$, when $R_3$ is other than hydrogen and the carbon atom marked with a double asterisk "**" is chiral when $R_1$ and $R_2$ are different. Thus the compounds of formula (I) can exist in up to 8 optical isomers. The present invention extends to all such isomers whether as individual isomers or as mixtures thereof in any proportion, including racemates.

The compounds of formula (I) may also exist in geometrical isomeric forms all of which are encompassed by the present invention, and including those wherein the $R_8.N.R_7$ moiety and $R_3$ are disposed either mutually trans with respect to one another or mutually cis with respect to one another.

Suitably, the $R_8.N.R_7$ moiety is trans to $R_3$.

Suitable alkyl groups or 'alkyl' moieties include straight or branched chain alkyl groups comprising up to 12 carbon atoms, suitable from 1 to 6 carbon atoms.

Suitable $C_{1-6}$ alkyl groups or $C_{1-6}$ alkyl moieties may be selected from methyl, ethyl, n- and iso-propyl, n-, iso-, sec- and tert-butyl.

Suitable polymethylene groups are $C_{3-8}$ polymethylene groups including $C_3$, $C_4$, $C_5$, $C_6$ and $C_7$ polymethylene groups.

Suitable acyloxy groups are $C_{1-7}$ acyloxy groups.

The term 'halogen' refers to fluorine, chlorine, bromine or iodine, suitably chlorine.

The present invention also provides a process for the preparation of a compound of formula (I) or, where appropriate a pharmaceutically acceptable salt thereof, or a pharmaceutically acceptable solvate thereof, which comprises reacting a compound of formula (II):

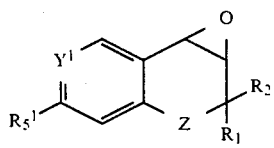

(II)

wherein $R_1$, $R_2$ and Z are as hereinbefore defined in relation to formula (I), $R_5^1$ represents $R_5$ or a group or atom convertible into $R_5$ and $Y^1$ represents Y or a group convertible into Y, with an activated form of a pyridone of formula (III):

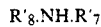

(III)

wherein $R'_7$ and $R'_8$ and the —NH— group to which they are attached form a substituted or unsubstituted pyridone, and thereafter if required, carrying out one or more of the following optional steps:
(i) converting a compound of formula (I) into a further compound of formula (I);
(ii) removing any protecting group;
(iii) converting $Y^1$ to Y;
(iv) converting $R_5^1$ to $R_5$;
(v) forming a pharmaceutically acceptable salt of the compound of formula (I); or
(vi) forming a pharmaceutically acceptable solvate of the compound of formula (I) or of the pharmaceutically acceptable salt thereof.

A suitable activated form of a compound of formula (III) is an ionic form. Thus in the reaction between a compound of formula (II) and a compound of formula (III), it is preferred that the reaction is carried out under basic conditions so as to facilitate the formation of the anion of the compound of formula (III), for example, in the presence of an alkali metal base such as potassium t-butoxide or sodium hydride or a base such as tetrabutylammonium fluoride.

The reaction between the compounds of formula (II) and (III) may be carried out in any suitable aprotic solvent, for example dimethylsulphoxide or tetrahydrofuran, at a temperature that provides a convenient rate of formation of the compound of formula (I), such as at ambient temperature or at an elevated temperature, conveniently at ambient temperature.

Suitably $R_5^1$ represents $R_5$. Suitably $Y^1$ represents Y.

Where appropriate the compound of formula (III) may itself be used as the solvent for the reaction between compounds of formulae (II) and (III).

Suitable conversions of a compound of formula (I) to a further compound of formula (I) include:
(i) converting $R_3$ in the resulting compound of formula (I) into another $R_3$;
(ii) converting a compound of formula (I) wherein $R_3$ and $R_4$ represent hydroxy and hydrogen respectively to give another compound of formula (I), wherein $R_3$ and $R_4$ together represent a bond;
(iii) reducing any compound of formula (I) wherein $R_3$ and $R_4$ together represent a bond; to give another compound of formula (I), wherein $R_3$ and $R_4$ each represent hydrogen; or
(iv) thiating a compound of formula (I) wherein $R_8.N.R_7$ represents a pyridonyl group to provide a compound of formula (I) wherein $R_8.N.R_7$ represents a thiopyridonyl group.

Examples of an optional conversion of $R_3$ in a compound of formula (I) into another $R_3$ are generally known in the art. For example, when $R_3$ is hydroxy, it may be alkylated using an alkyl iodide in an inert solvent, such as toluene, in the presence of a base, such as sodium hydride, or it may be acylated using a carboxylic acid chloride or the appropriate anhydride in a non-hydroxylic solvent, such as toluene or dichloromethane, in the presence of an acid acceptor such as triethylamine. Alternatively, when $R_3$ is $C_{1-6}$ alkoxy, it may be converted into hydroxy by any suitable dealkylation technique, for example by treatment with trimethylsilyliodide in an aprotic solvent. Also when $R_3$ is $C_{1-7}$ acyloxy it may be converted into hydroxy by conventional hydrolysis using, for example a dilute mineral acid.

The optional conversion of a compound of formula (I), wherein $R_3$ and $R_4$ are hydroxy and hydrogen respectively, into another compound of formula (I), wherein $R_3$ and $R_4$ together are a bond, may be carried out by dehydration under conventional dehydration conditions, for example, by using a dehydrating agent, such as sodium hydride, in inert solvent, such as dry tetrahydrofuran, at reflux temperature; alternatively the hydroxy group represented by $R_3$ may be converted into a leaving group such as a mesyloxy or tosyloxy group and the resulting compound treated with a base such as sodium hydride to provide the compound of formula (I) wherein $R_3$ and $R_4$ together represent a bond.

The reduction of a compound of formula (I), wherein $R_3$ and $R_4$ together are a bond, into another compound of formula (I), wherein $R_3$ and $R_4$ are each hydrogen, may be carried out by hydrogenation using a catalyst of palladium on charcoal.

The thiation of the $R_8.N.R_7$ group in a compound of formula (I) is suitably carried out with conventional thiation agents, such as hydrogen sulphide, phosphorus pentasulphide and Lawesson's reagent (p-methoxyphenylthiophosphine sulphide dimer).

The use of hydrogen sulphide and phosphorus pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is, preferably, carried out under reflux in a dry solvent, such as toluene or methylene chloride.

A compound of formula (II) may be prepared by reaction of a compound of formula (IV):

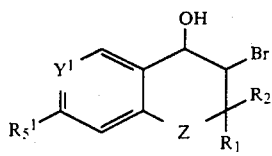

wherein $R_1$, $R_2$, $R_5^1$, $Y^1$ and Z are as hereinbefore defined, the bromine atom being trans to the hydroxy group, with a base, such as potassium hydroxide, in a solvent, such as ether or aqueous dioxan.

A compound of formula (IV) may be prepared by reaction of a compound of formula (V):

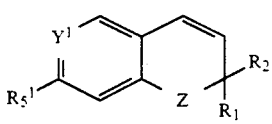

wherein $R_1$, $R_2$, $R_5^1$ and $Y^1$ are as hereinbefore defined, with N-bromosuccinimide in a solvent, such as aqueous dimethyl sulphoxide.

A compound of formula (II) wherein Y represents $CR_6$, may also be prepared directly from a compound of the hereinbefore defined formula (V), by reacting the compound of formula (V) with a per-acid, preferably a perbenzoic acid, and in particular with meta-chloroperbenzoic acid.

The reaction between the compound of formula (V) and the per-acid may be carried out in any suitable inert solvent such as dichloromethane at any suitable temperature, conveniently at ambient temperature.

A compound of formula (II), wherein Y represents N or $N^+$—$O^-$ and Z represents $CH_2$ may also be prepared by reacting together an appropriate azadiene and an appropriate cyclic enone in a Diels Alder reaction (using conventional Diels Alder conditions, for example those disclosed in J. Amer. Chem. Soc. 1975, (97), 4409) to provide an appropriate bicyclic ketone which may then be converted by further conventional chemistry to the said compound of formula (II).

The appropriate compounds of formula (II), (IV) and (V) may also be prepared according to procedures contained in the abovementioned published European patent applications.

The intermediates of formula (III) are known commercially available compounds or they may be prepared using conventional procedures.

Suitable protecting groups are those conventional protecting groups that may be prepared and removed using known procedures and which protect the appropriate chemical group during the preparation of compounds of formula (I)

Any conversion of $Y^1$ to Y or $R_5^1$ to $R_5$ may be carried out using the appropriate conventional chemical procedure.

The optional formation of a pharmaceutically acceptable salt, when the resulting compound of formula (I) contains a salifiable group, may be carried out conventionally. Similarly, pharmaceutically acceptable solvates, for example hydrates, may be prepared using any convenient conventional procedure.

As mentioned previously, some of the compounds of formula (I) may exist in optically active forms, and the processes of the present invention produce mixtures of such forms. The individual enantiomers may be resolved by conventional methods.

It is preferred that the compounds of formula (I) are isolated in substantially pure form.

The compounds of formula (I), the pharmaceutically acceptable salts thereof or the pharmaceutically acceptable solvates thereof, have been found to have bronchodilator activity and/or blood-pressure lowering activity. They are therefore useful in the treatment of respiratory tract disorders, such as reversible airways obstruction, diverticular disease and asthma and also hypertension. They may also be of potential use in the treatment of other disorders hereinbefore described.

The present invention accordingly provides a pharmaceutical composition which comprises a compound of formula (I), or, where appropriate, a pharmaceutically acceptable salt thereof or a pharmaceutically acceptable solvate thereof, and a pharmaceutically acceptable carrier.

The said compositions are preferably adapted for oral administration. However, they may be adapted for other modes of administration, for example in the form of a spray, aerosol or other conventional method for inhalation, for treating respiratory tract disorders and disorders associated with pulmonary hypertension or disorders associated with right heart failure; or parenteral administration for patients suffering from heart failure. Other alternative modes of administration include sublingual or transdermal administration. The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating. Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The comound can be sterilized by exposure to ethylene oxide before suspending in the sterile vehicle. Advantageously, a surfactant or wetting agent is included in the composition to facilitate uniform distribution of the compound.

As has been indicated above, certain of the compounds of formula (I)—in fact the compounds of the abovedefined formula (IA)—have been discovered to be of particular value in the treatment of reversible airways obstruction and asthma, especially asthma.

Accordingly, the present invention further provides a method for the treatment of reversible airways obstruction and asthma, especially asthma, in mammals, including humans, which method comprises the administration to the mammal in need thereof, a compound of the abovedefined formula (IA), or, where appropriate, a pharmaceutically acceptable salt thereof, or a pharmaceutically acceptable solvate thereof.

The present invention also provides the use of a compound of the abovedefined formula (IA) or, where appropriate, a pharmaceutically acceptable salt thereof, or a pharmaceutically acceptable solvate thereof, for the manufacture of a medicament for the treatment of reversible airways obstruction and asthma, especially asthma.

The invention further provides a composition for the treatment of reversible airways obstruction and asthma, especially asthma, which composition comprises a compound of the abovedefined formula (IA) or, where appropriate, a pharmaceutically acceptable salt thereof, or a pharmaceutically acceptable solvate thereof, and a pharmaceutically acceptable carrier therefore.

Suitable modes of administration and the appropriate forms of compositions used in the administration of the compounds of formula (IA) are, of course, equivalent to those indicated above. However, in a preferred aspect the abovementioned treatment of reversible airways obstruction and asthma comprises inhaled administration and thus comprises the use of a composition (or medicament) formulated for inhaled administration.

Suitably, compositions of this invention, in particular the said compositions used in the treatment of reversible airways obstruction and asthma, are presented for administration to the respiratory tract as a snuff or an aerosol or solution for a nebulizer, or as a microfine powder for insufflation alone or in combination with an inert carrier such as lactose.

Suitable solutions for a nebulizer are isotonic sterilised solutions, optionally buffered, at for example between pH 4-7, containing up to 20 mg ml$^{-1}$ of compound but more generally 0.1 to 10 mg ml$^{-1}$, for use with standard nebulisation equipment.

Accordingly, in one further aspect of the present invention, there is provided a compound of the abovedefined formula (IA) or, where appropriate, a pharmaceutically acceptable salt thereof, or a pharmaceutically acceptable solvate thereof, in the form of a microfine powder. As indicated such a powder is of particular value in administration via insufflation.

Accordingly, the present invention further provides a pharmaceutical composition, in particular a composition for inhaled administration, which comprises a compound of the abovedefined formula (IA) or, where appropriate, a pharmaceutically acceptable salt thereof, or a pharmaceutically acceptable solvate thereof, in the form of a microfine powder and optionally a pharmaceutically acceptable carrier. Suitable carriers are those used conventionally in the art, for example lactose.

Microfine powder formulations may suitably be administered in an aerosol as a metered dose or by means of a suitable breath-activated device.

Suitable metered dose aerosol formulations comprise conventional prepellants, cosolvents, such as ethanol, surfactants such as oleyl alcohol, lubricants such as oleyl alcohol, desiccants such as calcium sulphate and density modifiers such as sodium chloride.

The particles of active compound suitable have diameters of less than 50 microns, preferably less than 10 microns. For example particles of diameters in the range 1-50 microns, 1-10 microns or 1-5 microns are envisaged.

Where appropriate, small amounts of other antiasthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

The present invention further provides a method of treatment of respiratory tract disorders or hypertension in mammals including man, which method comprises administering to the mammal in need thereof an effective, non-toxic amount of a compound of formula (I), or, where appropriate, a pharmaceutically acceptable salt thereof or a pharmaceutically acceptable solvate thereof.

In a further aspect, the present invention provides a method for the treatment of irritable bowel syndrome and diverticular disease; premature labour; incontinence; renal cholic and disorders associated with the passage of kidney stones and/or the treatment and or prophylaxis of disorders associated with pulmonary hypertension and of disorders associated with right heart failure in mammals including man, which method comprises administering to the mammal in need thereof an effective, non-toxic amount of either: a compound of the abovedefined formula (IA); or, alternatively, a compound selected from the group consisting of: trans-6-cyano-3,4-dihydro-2,2-dimethyl-4-(2(1H)-pyridon-1-yl)-2H-1-benzopyran-3-ol,6-cyano-2,2-dimethyl-4-(2(1H)-pyridon-1-yl)-2H-1-benzopyran, trans-3,4-dihydro-2,2-dimethyl-6-trifluoromethyl-4-(2(1H)-pyridon-1-yl)-2H-1-benzopyran-3-ol and 2,2-dimethyl-6-trifluoromethyl-4-(2(1H)-pyridon-1-yl)-2H-1-benzopyran and trans-6-cyano-3,4-dihydro-2,2-dimethyl-4-(6(1H)-pyrimidon-1-yl)-2H-1-benzopyran-3-ol; or, where appropriate, a pharmaceutically acceptable salt thereof, or a pharmaceutically acceptable solvate thereof.

The present invention also provides the use of either: a compound of the abovedefined formula (IA); or, alternatively, a compound trans-6-cyano-3,4-dihydro-2,2-dimethyl-4-(2(1H)-pyridon-1-yl)-2H-1-benzopyran-3-ol,6-cyano-2,2-dimethyl-4-(2(1H)pyridon-1-yl)-2H-1-benzopyran, trans-3,4-dihydro-2,2-dimethyl-6-trifluoromethyl-4-(2(1H)-pyridon-1-yl)-2H-1-benzopyran-3-ol and 2,2-dimethyl-6-trifluoromethyl-4-(2(1H)-pyridon-1-yl)-2H-1-benzopyran or trans-6-cyano-3,4-dihydro-2,2-dimethyl-4-(6(1H)-pyrimidon-1-yl)-2H-1-benzopyran-3-ol; or, where appropriate, a pharmaceutically acceptable salt thereof, or a pharmaceutically acceptable solvate thereof, for the manufacture of a medicament for the treatment of irritable bowel syndrome and diverticular disease; premature labour; incontinence; renal cholic and disorders associated with the passage of kidney stones and/or disorders associated with pulmonary hypertension and of disorders associated with right heart failure.

The compositions may contain from 0.1% to 99% by weight, suitably 10-99% preferably from 10-60% by weight, of the active material, depending on the method of administration, thus a preferred range for inhaled administration is 10-99%, especially 60-99% for example 90, 95, or 99%.

An effective amount will depend on the relative efficacy of the compounds of the present invention, the severity of the respiratory tract disorder or hypertension being treated and the weight of the sufferer. However, a unit dose form of a composition of the invention may contain from 0.01 to 100 mg of a compound of the invention and more usually from 0.1 to 50 mg, for example 0.5 to 25 mg such as 1, 2, 5, 10, 15 or 20 mg. Inhalation doses suitably comprise 0.01 to 10 mg of active compound, favourably 0.05 to 0.5 mg. Such compositions may be administered from 1 to 6 times a day, more usually from 1 to 4 times a day, in a manner such that the daily dose is from 0.02 to 200 mg for a 70 kg human adult and more particularly from 0.05 to 100 mg. Effective amounts for the other indications mentioned above are analogous to those mentioned above.

No toxicological effects are indicated at the aforementioned dosage ranges.

The present invention further provides a compound of formula (I) or a pharmaceutically acceptable salt thereof, or, where appropriate, a pharmaceutically acceptable solvate thereof, for use as an active therapeutic substance.

The present invention further provides a compound of formula (I) or, where appropriate, a pharmaceutically acceptable salt thereof, or a pharmaceutically acceptable solvate thereof, for use in the treatment of respiratory tract disorders or hypertension.

The present invention further provides the use of a compound of formula (I), or, where appropriate, a pharmaceutically acceptable salt thereof, or a pharmaceutically acceptable solvate thereof for the manufacture of a medicament for the treatment of respiratory tract disorders or hypertension.

The following Examples illustrate the invention but do not limit it in any way.

EXAMPLE 1

Trans-6-Cyano-3,4-dihydro-2,2-dimethyl-4-(2(1H)-pyridon-1-yl)-2H-1-benzopyran-3-ol

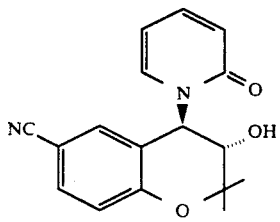

and

EXAMPLE 2

6-Cyano-2,2-dimethyl-4-(2(1H)-pyridon-1-yl)-2H-1-benzopyran

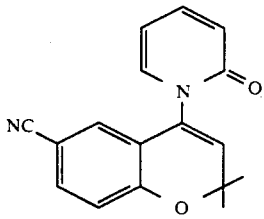

Sodium hydride (0.090 g, 6.25 mmol of a 60% dispersion in oil) was added to a stirred solution of 6-cyano-3,4-dihydro-2,2-dimethyl-3,4-epoxy-2H-1-benzopyran (0.402 g, 2.0 mmol) and 2-pyridone (0.190 g, 2.0 mmol) in dry dimethylsulphoxide (5 ml) under nitrogen at ambient temperature. The reaction mixture was allowed to stir for 30 h and then poured into water. The solution was extracted with ethyl acetate (×3) and the combined organic layers washed successively with water (×3) and brine. The organic phase was dried (MgSO$_4$), filtered and evaporated under reduced pressure to give an oil (0.520 g) which was chromatographed on silica. Elution with chloroform gave starting epoxide (0.074 g, 18%) followed by 6-cyano-4-(2(1H)-pyridon-1-yl)-2,2-dimethyl-2H-1-benzopyran (0.121 g, 22%), trans 6-cyano-3,4-dihydro-2,2-dimethyl-4-(2(1H)-pyridon-1-yl)-2H-1-benzopyran-3-ol (0.081 g, 14%) and trans 6-cyano-3,4-dihydro-2,2-dimethyl-2H-1-benzopyran-3,4-diol (0.120 g, 27%).

The benzopyran-3-ol (Example 1) was triturated with ether to give white solid (0.038 g), m.p. 240°-244° C. (sublimes from 230° C.).

$^1$Hnmr (CDCl$_3$) δ:1.37 (3H, s), 1.56 (3H, s), 3.86 (1H, dd, J=5, 9.9 Hz, collapses to a d J=9.9 Hz with D$_2$O), 4.15 (1H, d, J=5 Hz, disappears with D$_2$O), 6.28 (1H, m), 6.34 (1H, d, J=9.9 Hz), 6.69 (1H, d, J=8 Hz), 6.90 (1H, dd, J=1.7, 7.2 Hz), 6.98 (1H, dd, J=1.7, 7.2 Hz), 7.10 (1H, s), 7.39–7.46 (1H, m), 7.50 (1H, dd, J=1.4 Hz, 8 Hz).

Anal: Found C, 68.53; H, 5.72; N, 9.08%. $C_{17}H_{16}N_2O_3$ requires C, 68.90; H, 5.44; N, 9.46%.

The benzopyran (Example 2) was triturated with ether to give a white solid (0.063 g), m.p. 149°–151° C.

$^1$Hnmr (CDCl$_3$) δ:1.57 (3H, s), 1.62 (3H, s), 5.81 (1H, s), 6.28 (1H, m), 6.67 (1H, d, J=9 Hz), 6.94 (2H, m), 7.15 (1H, m) 7.43–7.51 (2H, m).

Anal: Found C, 73.46; H, 5.21; N, 10.07%. $C_{17}H_{14}N_2O_2$ requires C, 73.36; H, 5.07; N, 10.07%.

EXAMPLE 3

6-Cyano-2,2-dimethyl-4-(4(1H)-pyridon-1-yl)-2H-1-benzopyran

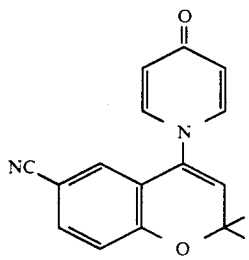

Potassium t-butoxide (0.282 g, 2.52 mmol) was added to a stirred solution of 6-cyano-3,4-dihydro-2,2-dimethyl-3,4-epoxy-2H-1-benzopyran (0.506 g, 2.52 mmol) and 4-pyridone (0.239 g, 2.52 mmol) in dry dimethyl sulphoxide (5 ml) under nitrogen at ambient temperature. The reaction mixture was allowed to stir for 7 days then poured into water and the aqueous layer extracted with ethyl acetate (×3) and chloroform (×3). The organic layers were washed with water, combined, dried, filtered and evaporated to give a yellow oil which was chromatographed on silica. Elution with methanol: chloroform (3:97) gave an oil which was re-chromatographed on alumina. Elution with chloroform gave an oil (0.372 g) consisting of the title compound contaminated with dimethyl sulphoxide. The oil was taken up in ethyl acetate, washed with water (×3), dried, filtered and evaporated to an oil (0.080 g) which was triturated with ether and filtered to give 6-cyano-2,2-dimethyl-4-(4(1H)-pyridon-1-yl)-2H-1-benzopyran, (0.041 g), (6%), m.p. 198°–203° C.

$^1$H nmr (CDCl$_3$) δ:1.58 (6H, s), 5.84 (1H,s), 6.48 (2H, d, J=7.7 Hz), 6.99 (1H, d, J=8.2 Hz), 7.13 (1H, d, J=1.9 Hz), 7.30 (2H, d, J=7.7 Hz), 7.55 (1H, dd, J=1.9 and 8.2 Hz).

Anal: Found C, 72.80; H, 5.62; N, 9.80%; $C_{17}H_{14}N_2O_2$ requires C, 73.36; H 5.07; N 10.07%.

EXAMPLE 4

Trans-3,4-Dihydro-2,2-dimethyl-6-trifluoromethyl-4-(2(1H)-pyridon-1-yl)-2H-1-benzopyran-3-ol

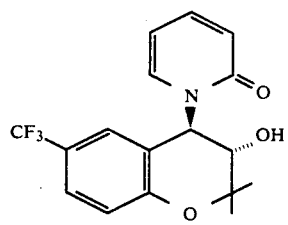

and

EXAMPLE 5

2,2-Dimethyl-6-trifluoromethyl-4-(2(1H)-pyridon-1-yl)-2H-1-benzopyran

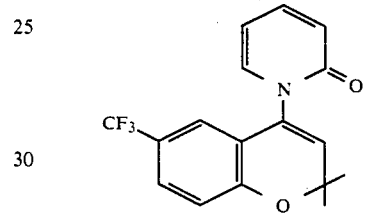

Potassium tert-butoxide (0.56 g, 1 eq) was added to a stirred solution of 3,4-dihydro-2,2-dimethyl-3,4-epoxy-6-trifluoromethyl-2H-1-benzopyran (0.98 g, 4 mmol) and 2-pyridone (0.48 g, 1.25 eq) in dry dimethylsulphoxide (1.5 ml) under nitrogen at ambient temperature. The reaction mixture was allowed to stir for 24 hours and was then poured into dilute hydrochloric acid (50 ml). The solution was extracted with diethyl ether (200 ml) and the organic layer washed with water (30 ml). The organic phase was dried (MgSO$_4$), filtered and evaporated under reduced pressure to give an oil (1.41 g) which was chromatographed on silica. Elution with a gradient from hexane to ether gave 2,2-dimethyl-6-trifluoromethyl-4-(2(1H)-pyridon-1-yl)-2H-1-benzopyran (0.272 g, 20.5%) followed by trans-3,4-dihydro-2,2-dimethyl-6-trifluoromethyl-4-(2(1H)-pyridon-1-yl)-2H-1-benzopyran-3-ol (0.336 g, 24%).

The benzopyran-3-ol (Example 4) was obtained as a white solid, m.p. 178°–182° C.

1HNMR (CDCl$_3$) δ:1.36 (3H,s), 1.55 (3H,s), 3.88 (1H,dd,J=5,9.6 Hz), 4.37 (1H,d,J=5 Hz), 6.26 (1H,m), 6.36 (1H,d,J=9.9 Hz), 6.68 (1H,d,J=9 Hz), 6.9–7.01 (3H,m), 7.37–7.49 (2H,m).

ANALYSIS: Found C: 60.07, H: 4.77, N: 4.25%. $C_{17}H_{16}NO_3F_3$ requires C: 60.17, H: 4.75, N: 4.13%.

The benzopyran (Example 5) was obtained as a white solid, m.p. 126°–129° C.

1HNMR (CDCl$_3$) δ:1.56 (3H,s), 1.61 (3H,s), 5.79 (1H,s), 6.26 (1H,m,), 6.66 (1H,d,J=9.5 Hz), 6.92 (2H,m), 7.16 (1H,m), 7.26–7.49 (2H,m).

ANALYSIS: Found C: 63.55, H: 4.37, N: 4.50%. $C_{17}H_{14}NO_2F_3$ requires C: 63.55, H: 4.39, N: 4.36%.

EXAMPLE 6

Trans-3,4-Dihydro-2,2-dimethyl-4-(2(1H)-pyridon-1-yl)-2H-pyrano[3,2-c]pyridine-3-ol)

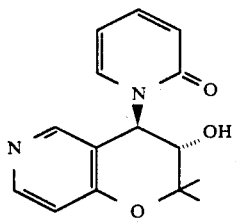

2-Pyridone (0.57 g, 6 mmol) in tetrahydrofuran (THF) (15 ml) was added to potassium hydride (0.24 g, 0.7 g of 35% suspension in oil washed with n-hexane) in THF (10 ml) at 0° C. After 30 minutes 3,4-dihydro-2,2-dimethyl-3,4-epoxy-2H-pyrano[3,2-c]pyridine (0.8 g, 4.5 mmol) in THF (5 ml) was added followed by 18-crown-6 (0.1 g). The mixture was stirred under nitrogen at 20° C. for 48 hours after which time it was added to water (25 ml). The solution was extracted with ethyl acetate (200 ml) and the organic layer washed with brine (25 ml). After drying (MgSO₄) the organic layer was evaporated under reduced pressure to give a solid (1.1 g) which was chromatographed on silica (eluting with a dichloromethane to acetone gradient) to give trans-3,4-dihydro-2,2-dimethyl-4-(2-pyridyloxy)-2H-pyrano[3,2-c]pyridine-3-ol) (0.04 g, 3%), followed by the epoxide substrate (0.098 g, 12%), followed by trans-3,4-dihydro-2,2-dimethyl-4-(2(1H)-pyridon-1-yl)-2H-pyrano[3,2-c]pyridine-3-ol) (0.53 g, 43%) as a solid, m.p. 207° C. with decomposition.

IR (KBr): 3405(s), 1660(s), 1585(s).

¹HNMR (CDCl₃) δ:1.38 (3H,s), 1.55 (3H,s) 3.86 (1H,d, J=9.9 Hz), 4.93 (1H,br), 6.26 (1H,t, J=6.7 Hz), 6.39 (1H,d, J=9.9 Hz), 6.64 (1H,d, J=9.1 Hz), 6.80 (1H,d, J=5.8 Hz), 6.98 (1H,dd, J=1.7 Hz, J=6.9 Hz), 7.33-7.4 (1H,m), 7.91 (1H,s) and 8.30 (1H,d, J=5.8 Hz).

Anal: Found C, 66.21; H,5.79; N,10.06%; $C_{15}H_{16}N_2O_3$ requires C,66.16; H,5.92; N,10.29%.

EXAMPLE 7

2,2-Dimethyl-4-(2(1H)-pyridon-1-yl)-2H-pyrano[3,2-c]pyridine

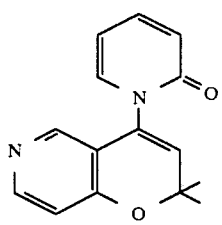

Sodium hydride (0.08 g, 1.5 eq, 80% dispersion in oil) was added to trans-3,4-dihydro-2,2-dimethyl-4-(2(1H)-pyridon-1-yl)-2H-pyrano[3,2-c]pyridine-3-ol) (0.60 g, 2.2 mmol) in tetrahydrofuran (THF) (50 ml). The resulting mixture was stirred at 60° C. under nitrogen for 48 hours and was then poured into water (50 ml) and basified with sodium hydroxide (1M). The solution was extracted with ethyl acetate (250 ml) and the organic layer dried (MgSO₄) and evaporated under reduced pressure. Chromatography of the residue on silica (2% MeOH/CHCl₃) yielded 2,2-dimethyl-4-(2(1H)-pyridon-1-yl)-2H-pyrano[3,2-c]pyridine) (0.465 g, 83%) as a solid, m.p. 120°-121° C.

IR (Nujol): 1675 (s), 1605 (s).

¹HNMR (CDCl₃) δ:1.57 (3H,s), 1.63 (3H,s), 5.74 (1H,s), 6.26 (1H,t, J=6.7 Hz), 6.66 (1H,d, J=9.4 Hz), 6.76 (1H,d,5.5 Hz), 7.18 (1H,dd, J=1.9 Hz, J=6.9 Hz), 7.40-7.48 (1H,m), 7.87 (1H,s) and 8.30 (1H,d, J=5.3 Hz).

Anal: Found C, 70.66; H,5.42; N,11.03%; $C_{15}H_{14}N_2O_2$ requires C,70.85; H,5.55; N,11.02%.

EXAMPLE 8

2,2-Dimethyl-4-(2(1H)-pyridon-1-yl)-2H-pyrano[3,2-c]pyridine

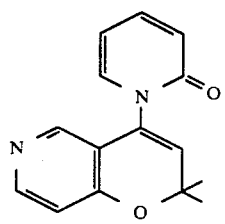

Trans-3,4-dihydro-2,2-dimethyl-3-methanesulphonyloxy-4-(2(1H)-pyridon-1-yl)-2H-pyrano[3,2-c]pyridine (3.43 g, 9.8 mmole) and sodium hydride (0.28 g, 0.35 g of 80% dispersion in oil, 1.2 eq) were stirred vigorously in tetrahydrofuran (THF, 150 ml) under nitrogen at room temperature for 18 hours. After adding more sodium hydride (0.03 g of 80% dispersion) and stirring for a further 18 hours TLC showed no starting material remained. The mixture was filtered and the solvent removed under reduced pressure to give a slightly yellow solid (2.52 g) which was recrystallized from ethyl acetate to give 2,2-dimethyl-4-(2(1H)-pyridon-1-yl)-2H-pyrano[3,2-c]pyridine (2.4 g, 96%) as a white solid, m.p. 120.5°-121° C. The material was identical to material obtained in Example 7.

EXAMPLE 9

Trans-3,4-Dihydro-2,2-dimethyl-4-(4(1H)-pyrimidinon-1-yl)-2H-pyrano[3,2-c]pyridine-3-ol

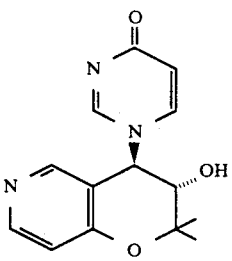

4(3H)-Pyrimidone (0.480 g, 5 mmol), tetrabutylammonium fluoride trihydrate (1.26 g, 4 mmol) and 3,4-dihydro-2,2-dimethyl-3,4-epoxy-2H-pyrano[3,2-c]pyridine (0.720 g, 3.8 mmol) were combined with dry tetrahydrofuran (20 ml) and stirred for four days at ambient temperature. The solvent was removed and the residue chromatographed on silica (chloroform to chloroform/methanol, 4:1). Unreacted epoxide and 4(3H)-pyrimidone were eluted followed by trans-3,4-dihydro-2,2- dimethyl-4-(4(1H)-pyrimidinon-1-yl)-2H-pyrano[3,2-c]pyridine-3-ol, m.p. 291° C. decomp. (MeOH).

¹HNMR (d₆-DMSO) δ:1.22 (3H, s), 1.46 (3H,s), 3.8 (1H, m), 5.23 (1H, d, J=10 Hz), 6.02 (1H, d, J=7.7 Hz), 6.19 (1H, d, J=6.0 Hz), 6.88 (1H, d, J=5.5 Hz), 7.63 (1H, dd, J₁=7.7 Hz, J₂=2.5 Hz), 8.00(1H, s), 8.30 (1H, d, J=5.5 Hz), 8.45 (1H, d, J=2.5 Hz).

IR(Nujol): 3200 (b), 1640, 1615, 1595, 1305, 1280, 925, 840 cm⁻¹.

Mass spectrum: observed, 273.1118. C₁₄H₁₅N₃O₃ required, 273.1113.

This example was also prepared by heating an equimolar mixture of 4(3H)-pyrimidone and 3,4-dihydro-2,2-dimethyl-3,4-epoxy-2H-pyrano[3,2-c]pyridine at 60° C. for 1 hour followed by chromatography as above.

EXAMPLE 10

Trans-6-Cyano-3,4-dihydro-2,2-dimethyl-4-(6(1H)pyrimidinon-1-yl)-2H-1-benzopyran-3-ol

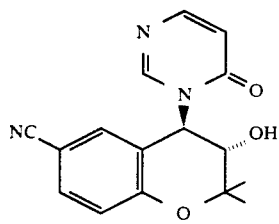

4(3H)-Pyrimidone (0.772 g, 8 mmol) was dissolved in dimethylsulphoxide (10 ml) and treated with potassium tert-butoxide (0.440 g, 4 mmol). The mixture was stirred for 30 minutes at ambient temperature and 6-cyano-3,4-dihydro-2,2-dimethyl-3,4-epoxy-2H-1-benzopyran (1.278 g, 6 mmol) added. The resulting mixture was heated at 90° C. for 30 minutes, cooled and poured into water. Extractive work up with ethyl acetate yielded a gum which was purified by chromatography on silica (ethyl acetate) to give trans-6-cyano-3,4-dihydro-2,2-dimethyl-4-(6(1H)-pyrimidinon-1-yl)-2H-1-benzopyran-3-ol 0.703 g, (38%), mpt 202°-3° (ethyl acetate/hexane).

¹H NMR (d₆-DMSO, 120° C.) δ:1.25 (3H,s), 1.48 (3H,s), 4.25 (1H,m), 5.35 (1H, bs), 5.60 (1H, d J=5 Hz), 6.35 (1H,d, J=6 Hz), 6.95 (1H,d, J=9 Hz), 7.18 (1H,s), 7.53 (1H,dd, J₁=9 Hz, J₂=2 Hz), 7.90 (1H,d, J=6 Hz), 8.35 (1H,s).

IR (Nujol) 3280(b), 2220, 1700, 1600, 1200, 1135, 1060, 950, 830 cm⁻¹.

Analysis: Found C, 65.01; H,5.04; N,140.3%. C₁₆H₁₅N₃O₃ requires C,64.64; H,5.09; N,14.13%.

EXAMPLE 11

Trans-3,4-Dihydro-2,2-dimethyl-4-(2(1H)-pyrimidon-1-yl)-2H-pyrano[3,2-c]pyridine-3-ol

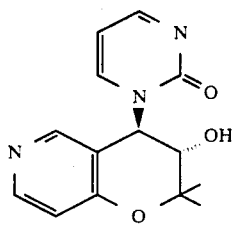

2(1H)-Pyrimidone (0.134 g, 1.4 mmol) was combined with 3,4-dihydro-2,2-dimethyl-3,4-epoxy-2H-pyrano[3,2-c]-pyridine (0.25 g, 1.32 mmol). The mixture was heated at 70° C. under nitrogen for 90 minutes, cooled and purified by chromatography on silica (CHCl₃/MeOH, 4:1) to give trans-3,4-dihydro-2,2-dimethyl-4-(2(1H)-pyrimidon-1-yl)-2H-pyrano[3,2-c]pyridine-3-ol (0.131 g), m.p. 256°-7° C. decomposition (ethyl acetate/MeOH).

IR (Nujol): 3200, 1650, 1635, 1600, 1590, 1580, 1565, 1530, 1175, 1130, 1085, 930, 825, 790 cm⁻¹.

¹H NMR (d₆-DMSO, 120° C.) δ:1.25 (3H,s), 1.48 (3H,s), 4.23 (1H,d, J=9.7 Hz), 5.47 (1H,bd,), 5.56 (1H,bs), 6.41 (1H,dd, J₁=6.6 Hz, J₂=4.1 Hz), 6.76 (1H,d, J=5.5 Hz), 7.84 (1H,d, J=0.6 Hz), 8.05 (1H,dd, J₁=6.6 Hz, J₂=2.8 Hz), 8.20 (1H,dd, J₁=5.5 Hz, J₂=0.6 Hz), 8.56 (1H,dd, J₁=4.1 Hz, J₂=2.8 Hz).

EXAMPLE 12

2,2-Dimethyl-4-(2(1H)-pyridon-1-yl)-2H-pyrano[3,2-c]pyridine, malonic acid salt

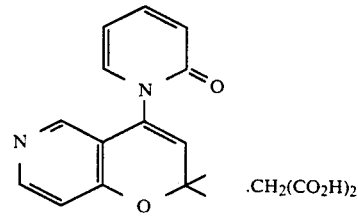

(E12)

2,2-Dimethyl-4-(2(1H)-pyridon-1-yl)-2H-pyrano[3,2-c]pyridine (0.254 g, 1 mmole) and powdered malonic acid (0.11 g, 1.1 eq) were stirred in chloroform (3 ml). After ½ hour all the solid had dissolved, the mixture was then stirred at room temperature overnight. Removal of the solvent gave a solid which rapidly picked up moisture to give a gum. Extraction of the residue with ethyl acetate followed by removal of the solvent at reduced pressure gave 2,2-dimethyl-4-(2(1H)-pyridon-1-yl)-2H-pyrano[3,2-c]-pyridine malonic acid salt as a hygroscopic solid (0.25 g, 71%).

IR: 2790(m), 2500(br), 1725(m), 1665(s), 1590(m), 1475(m), 1130(m), 900(m)cm⁻¹.

¹H NMR (CDCl₃) δ:1.68 (3H, s), 1.72 (3H, s), 3.25 (2H, s), 6.00 (1H, s), 6.42(1H, d, J=7.5 Hz), 6.70 (1H, d, J=9 Hz), 7.08 (1H, d, J=6 Hz), 7.35 (1H, d, J=6 Hz), 7.45-7.70 (1H, m), 8.02 (1H, s), 8.48 (1H, d, J=6 Hz), 14.53 (2H, s).

EXAMPLE 13

2,2-Dimethyl-4-(2(1H)-pyridon-1-yl)-2H-pyrano[3,2-c]pyridine-N-oxide

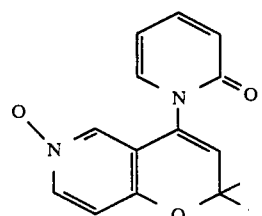

(E13)

2,2-Dimethyl-4-(2(1H)-pyridon-1-yl)-2H-pyrano[3,2-c]pyridine (0.254 g, 1 mmole) and m-chloroperbenzoic acid (55% grad, 0.32 g, 1eq) in chloroform (4 ml) were stirred at room temperature overnight. After removing the solvent at reduced pressure the residue was chromatographed on silica (CHCl₃, MeOH 19:1) to give 2,2-dimethyl-4-(2(1H)-pyridon-1-yl)-2H-pyrano[3,2-c]pyridine-N-oxide, (0.265 g, 98%), m.p.>180° C.(d).

IR (CHCl₃): 2785(m), 1665(s), 1590(m), 1440(m), 1265(m), 915(m); cm⁻¹.

1H NMR (CDCl₃) δ: 1.60 (3H, s), 1.66 (3H, s), 5.96(1H, s), 6.33 (1H, dt, $J_t=7.5$ Hz, $J_d=1.5$ Hz), 6.65 (1H, d, J=9 Hz), 6.84 (1H, d, J=7.5 Hz), 7.25 (1H, dd, J=7 Hz, J=1.5 Hz), 7.40–7.63 (1H, m), 7.70 (1H, s), 8.05 (1H, d, J=7 Hz).

EXAMPLE 14

Inhalation formulations (a) Solution for nebulisation

An isotonic sterilised solution of the active compound (10 mg ml⁻¹), pH7 is prepared according to standard procedures.

This solution may be used with conventional nebulisation equipment.

(b) Formulations for breath-actuated devices

The active compound is powdered in conventional manner to provide a microfine powder of particle size 1–5 microns. The powder is admixed with lactose in the proportions of 1:50 (active compound to lactose).

In an alternative formulation the active compound is used without lactose.

The formulations may be used with conventional breath actuated devices.

DESCRIPTION 1

Trans-3,4-Dihydro-2,2-dimethyl-3-methanesulphonyloxy-4-(2(1H)-pyridon-1-yl)-2H-pyrano[3,2-c]pyridine

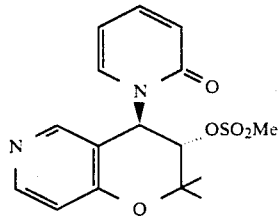

Triethylamine (3.72 ml, 2.7 g, 2 eq) and mesyl chloride (3.05 g, 2.05 ml, 2 eq) were slowly added, simultaneously, to a vigorously stirred suspension of the chromanol (3.633 g, 13.36 mmole) in tetrahydrofuran (THF, 50 ml) at room temperature under nitrogen. Following complete addition the reaction was stirred for a further 30 minutes when thin layer chromatography indicated that all of the starting material had been consumed. The mixture was added to chloroform (500 ml) and washed with water (50 ml). The aqueous phase was then extracted with chloroform (2×300 ml) and the combined organic phase was dried (MgSO₄) and evaporated. The solid residue (5.28 g) was chromatographed on silica (2% MeOH in CHCl₃) to yield trans-3,4-dihydro-2,2-dimethyl-3-methanesulphonyloxy-4-(2(1H)-pyridon-1-yl)-2H-pyrano[3,2-c]pyridine (3.78 g, 81%) as a white solid, m.p. 180°–181° C.

IR (Nujol): 1660(s), 1590(s), 1340(s), 1175(s), 1010(s), 970(s) and 940(s) cm⁻¹.

¹H n.m.r. (CDCl₃) δ: 1.45 (3H, s), 1.63 (3H, s), 2.89 (3H, s), 4.96 (1H, d, J=9.6 Hz), 6.26 (1H,t, J=6.6 Hz), 6.67 (1H,d, J=9.4 Hz), 6.74 (1H, J=9.9 Hz), 6.84 (1H, d, J=5.5 Hz), 6.97 (1H,dd, J=7.15 Hz, J=1.65 Hz), 7.38 (1H, complex multiplet), 8.01 (1H,s), 8.38 (1H,d, J=5.23 Hz).

PHARMACOLOGICAL DATA

1. Bronchodilator Activity (a) Bronchodilation in vitro; guinea pig tracheal spiral preparations Male guinea pigs (300–600 g) were stunned by a blow to the head and bled from the carotid artery. The trachea was exposed, dissected free of connective tissue, and transferred to oxygenated krebs solution at 37° C. Next, spirals (2 per trachea) were prepared by cutting the whole trachea spirally along its longitudinal axis and then dividing this spiral lengthwise. Each preparation was mounted, using silk thread, in a 10 ml organ bath filled with krebs solution at 37° C. and bubbled with 5% $CO_2$ with $O_2$. The resting tension of the preparations was set at 2 g and changes in muscle tension were monitored isometrically by means of a UFI (2 oz) force and displacement transducer (Ormed Ltd) connected to a Linseis pen recorder. All preparations were allowed to equilibrate for 60 minutes. During this equilibration period the preparations were washed by upward displacement at 15 minute intervals and, if necessary, the resting tension was readjusted to 2 g using a mechanical micromanipulator system.

Once a steady resting tension had been obtained, the preparations were dosed cumulatively with the test compound ($10^{-8}$–$2\times10^{-5}$M), and finally a maximum relaxation achieved by addition of $10^{-3}$M isoprenaline. The fall in tension evoked by the test compound was expressed as a percentage of the total relaxation evoked in the presence of $10^{-3}$M isoprenaline. Appropriate concentration-relaxation curves were then constructed and values for potency (IC₅₀) were obtained.

The composition of Krebs solution is: sodium chloride 118.07 mM, sodium hydrogen carbonate 26.19 mM, potassium chloride 4.68 mM, potassium orthophosphate 1.18 mM, magnesium sulphate septahydrate 1.8 mM and calcium chloride 2.52 mM; pH ca. 7.45.

| Compound of Example No: | Results | |
|---|---|---|
| | In vitro IC₅₀ value (M) | Intrinsic Activity |
| 1 | 7.9 × 10⁻⁷ | 0.96 |
| 2 | 1.0 × 10⁻⁷ | 0.92 |
| 3 | 1.1 × 10⁻⁵ | 0.75 |
| 4 | 5.4 × 10⁻⁷ | 0.95 |
| 5 | 5.2 × 10⁻⁸ | 0.99 |
| 6 | 5.5 × 10⁻⁶ | 0.81 |
| 7 | 2.4 × 10⁻⁶ | 0.93 |

2. Antihypertensive Activity

Blood Pressure Lowering Activity

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005 was used to display pulses. Prior to all measurements rats were placed in a heated environment (33.5°±0.5° C.) before transfer to a restraining cage. Each determination of blood pressure was the mean of at least 6 readings. Spontaneously hypertensive rats (ages 12–18 weeks) with systolic blood pressures > 180 mmHg were considered hypertensive.

| Example No | Dose (p.o) | Time, post dose (h) | % Change in Systolic B.P. (mmHg) |
|---|---|---|---|
| 1 | 0.1 mg/kg | 1 | $-12 \pm 5$ (n = 6) |
| (Initial Blood) | | 2 | $-20 \pm 2$ (n = 6) |
| (Pressure 247 $\pm$ 7) | | 4 | $-21 \pm 3$ (n = 6) |
| | | 6 | $-23 \pm 5$ (n = 4) |
| 2 | 0.03 mg/kg | 1 | $-34 \pm 4$ (n = 5) |
| (Initial Blood) | | 2 | $-41 \pm 3$ (n = 5) |
| (Pressure 265 $\pm$ 7) | | 4 | $-38$ (n = 2) |
| | | 6 | $-32 \pm 3$ (n = 2) |
| 3 | 3 mg/kg | 1 | $-46 \pm 7$ (n = 6) |
| (Initial Blood) | | 2 | $-49 \pm 3$ (n = 6) |
| (Pressure 257 $\pm$ 10) | | 4 | $-63$ (n = 6) |
| | | 6 | $-57 \pm 3$ (n = 6) |
| 4 | 0.3 mg/kg | 1 | $-37 \pm 7$ (n = 4) |
| (Initial Blood) | | 2 | $-42 \pm 3$ (n = 6) |
| (Pressure 227 $\pm$ 6) | | 4 | $-32 \pm 5$ (n = 2) |
| | | 6 | $-34$ (n = 1) |
| 5 | 0.03 mg/kg | 1 | $-15 \pm 3$ |
| (Initial Blood) | | 2 | $-20 \pm 1$ |
| (Pressure 236 $\pm$ 5) | | 4 | $-25 \pm 3$ |
| | | 6 | $-28 \pm 1$ |

We claim:

1. A pharmaceutical composition useful for the treatment of reversible airways obstruction and asthma in mammals including humans which comprises a therapeutically effective amount of a compound of the formula (IA):

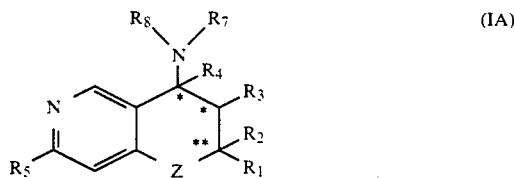
(IA)

a pharmaceutically acceptable salt thereof or a pharmaceutically acceptable solvate thereof, in the form of a microfine powder, wherein Z is O;

$R_1$ and $R_2$ are each hydrogen or alkyl of 1 to 6 carbon atoms; or $R_1$ and $R_2$ together are polymethylene;

$R_3$ is hydrogen, hydroxy, alkoxy of 1 to 6 carbon atoms or acyloxy of 1 to 7 carbon atoms; $R_4$ is hydrogen; or $R_3$ and $R_4$ together are a bond; $R_5$ is hydrogen; and $R_7$ and $R_8$ together with the nitrogen atom to which they are attached form a 6-membered unsubstituted or substituted, unsaturated heterocyclic ring, the ring being a single ring and having the depicted nitrogen atom as the sole heteroatom and wherein a carbon atom of the ring forms the moiety C=X wherein X is O or S, in combination with a pharmaceutically acceptable carrier.

2. A composition according to claim 1 wherein $R_8.N.R_7$ is 4-pyridon-1-yl.

3. A composition according to claim 1 wherein the compound is in the form of a solvate.

4. A composition according to claim 1 in inhalation administration form.

5. The composition according to claim 1, wherein the particles of said microfine powder have a particle size of less than 50 microns.

6. A composition according to claim 1 wherein the compound is Trans-3,4-dihydro-2,2-dimethyl-4-(2(1H)pyridon-1-yl)-2H-pyrano[3,2-c]pyridine-3-ol).

7. A composition according to claim 1 wherein the compound is 2,2-dimethyl-4-(2(1H)-pyridon-1-yl)-2H-pyrano[3,2-c]pyridine.

8. A composition according to claim 1 wherein the compound is 2,2-dimethyl-4-(2(1H)-pyridon-1-yl)-2H-pyrano[3,2-c]pyridine-N-oxide.

9. A composition according to claim 1 wherein $R_8.N.R_7$ is 2-pyridon-1-yl.

10. A method for the treatment of reversible airways obstructions and asthma in mammals including humans which comprises administering to such a mammal in need thereof a therapeutically effective amount of a compound of the formula (IA):

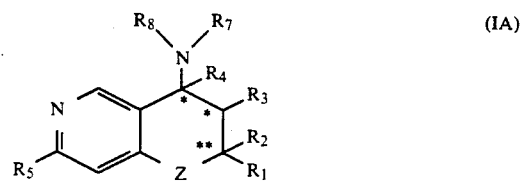
(IA)

a pharmaceutically acceptable salt thereof or a pharmaceutically acceptable solvate thereof, in the form of a microfine powder, wherein Z is O;

$R_1$ and $R_2$ are each hydrogen or alkyl of 1 to 6 carbon atoms; or $R_1$ and $R_2$ together are polymethylene;

$R_3$ is hydrogen, hydroxy, alkoxy of 1 to 6 carbon atoms or acyloxy of 1 to 7 carbon atoms; $R_4$ is hydrogen; or $R_3$ and $R_4$ together are a bond; $R_5$ is hydrogen; and $R_7$ and $R_8$ together with the nitrogen atom to which they are attached form a 6-membered unsubstituted or substituted, unsaturated heterocyclic ring, the ring being a single ring and having the depicted nitrogen atom as the sole heteroatom and wherein a carbon atom of the ring forms the moiety C=X wherein X is O or S, in combination with a pharmaceutically acceptable carrier.

11. A method according to claim 10 wherein $R_8.N.R_7$ is 4-pyridon-1-yl.

12. A method according to claim 10 wherein the compound is in the form of a solvate.

13. A method according to claim 10 in inhalation administration form.

14. A method according to claim 10 wherein the compound is Trans-3,4-dihydro-2,2-dimethyl-4-(2(1H)-pyridon-1-yl)-2H-pyrano[3,2-c]pyridine-3-ol).

15. A method according to claim 10 wherein the compound is 2,2-dimethyl-4-(2(1H)-pyridon-1-yl)-2H-pyrano[3,2-c]pyridine.

16. A method according to claim 10 wherein the compound is 2,2-dimethyl-4-(2(1H)-pyridon-1-yl)-2H-pyrano[3,2-c]pyridine-N-oxide.

17. A method according to claim 10 wherein $R_8.N.R_7$ is 2-pyridon-1-yl.

18. The method according to claim 10, wherein the particles of said microfine powder have a particle size of less than 50 microns.

19. A pharmaceutical composition useful for the treatment of reversible airways obstructions and asthma in mammals including humans which comprises a therapeutically effective amount of a compound of the formula (IA):

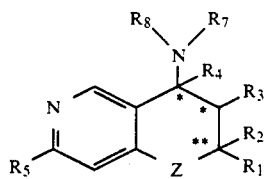 (IA)

a pharmaceutically acceptable salt thereof or a pharmaceutically acceptable solvate thereof, in the form of a microfine powder, wherein Z is O;

$R_1$ and $R_2$ are each hydrogen or alkyl of 1 to 6 carbon atoms; or $R_1$ and $R_2$ together are polymethylene;

$R_3$ is hydrogen, hydroxy, alkoxy of 1 to 6 carbon atoms or acyloxy of 1 to 7 carbon atoms; $R_4$ is hydrogen; or $R_3$ and $R_4$ together are a bond; $R_5$ is hydrogen; and $R_7$ and $R_8$ together with the nitrogen atom to which they are attached form a 6-membered unsubstituted or substituted, unsaturated heterocyclic ring, the ring being a single ring and having up to two nitrogen heteroatoms and wherein a carbon atom of the ring forms the moiety C=X wherein X is O or S, in combination with a pharmaceutically acceptable carrier.

20. A composition according to claim 19 wherein $R_8.N.R_7$ is 4(1H)-pyrimidinon-1-yl.

21. A composition according to claim 19 wherein the compound is Trans-3,4-dihydro-2,2-dimethyl-4-(4(1H)-pyrimidinon-1-yl)-2H-pyrano[3,2-c]pyridine-3-ol.

22. A composition according to claim 19 wherein the compound is Trans-3,4-dihydro-2,2-dimethyl-4-(2(1H)-pyrimidon-1-yl)-2H-pyrano[3,2-c]pyridine-3-ol.

23. A method for the treatment of reversible airways obstructions and asthma in mammals including humans which comprises administering to such a mammal in need thereof a therapeutically effective amount of a compound of the formula (IA):

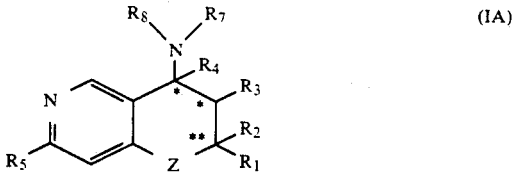 (IA)

a pharmaceutically acceptable salt thereof or a pharmaceutically acceptable solvate thereof, in the form of a microfine powder, wherein Z is O;

$R_1$ and $R_2$ are each hydrogen or alkyl of 1 to 6 carbon atoms; or $R_1$ and $R_2$ together are polymethylene;

$R_3$ is hydrogen, hydroxy, alkoxy of 1 to 6 carbon atoms or acyloxy of 1 to 7 carbon atoms; $R_4$ is hydrogen; or $R_3$ and $R_4$ together are a bond; $R_5$ is hydrogen; and $R_7$ and $R_8$ together with the nitrogen atom to which they are attached form a 6-membered unsubstituted or substituted, unsaturated heterocyclic ring, the ring being a single ring and having up to two nitrogen heteroatoms and wherein a carbon atom of the ring forms the moiety C=X wherein X is O or S, in combination with a pharmaceutically acceptable carrier.

24. A method according to claim 23 wherein $R_8.N.R_7$ is 4(1H)-pyrimidinon-1-yl.

25. A method according to claim 23 wherein the compound is Trans-3,4-dihydro-2,2-dimethyl-4-(4(1H)-pyrimidinon-1-yl)-2H-pyrano[3,2-c]pyridine-3-ol.

26. A method according to claim 23 wherein the compound is Trans-3,4-dihydro-2,2-dimethyl-4-(2(1H)-pyrimidon-1-yl)-2H-pyrano[3,2-c]pyridine-3-ol.

* * * * *